(12) United States Patent
Huschke

(10) Patent No.: US 10,018,536 B2
(45) Date of Patent: Jul. 10, 2018

(54) SMALL VOLUME SAMPLING DEVICE

(71) Applicant: SAINT-GOBAIN PERFORMANCE PLASTICS CORPORATION, Solon, OH (US)

(72) Inventor: Michael R. Huschke, Midland, MI (US)

(73) Assignee: SAINT-GOBAIN PERFORMANCE PLASTICS CORPORATION, Solon, OH (US)

( * ) Notice: Subject to any disclaimer, the term of this patent is extended or adjusted under 35 U.S.C. 154(b) by 113 days.

(21) Appl. No.: 15/085,709

(22) Filed: Mar. 30, 2016

(65) Prior Publication Data

US 2016/0313221 A1    Oct. 27, 2016

Related U.S. Application Data

(60) Provisional application No. 62/150,530, filed on Apr. 21, 2015.

(51) Int. Cl.
*G01N 1/14* (2006.01)

(52) U.S. Cl.
CPC ....... *G01N 1/14* (2013.01); *G01N 2001/1418* (2013.01)

(58) Field of Classification Search
None
See application file for complete search history.

(56) References Cited

U.S. PATENT DOCUMENTS

| | | | |
|---|---|---|---|
| 898,456 A | 9/1908 | Farnham | |
| 3,461,868 A | 8/1969 | Palich | |
| 3,938,392 A | 2/1976 | Rodrigues | |
| D250,599 S | 12/1978 | St. Amand | |
| D252,586 S | 8/1979 | Kovach | |
| D256,053 S | 7/1980 | Steigerwald | |
| 4,250,893 A * | 2/1981 | White | A61B 5/150022 |
| | | | 600/578 |
| D260,434 S | 8/1981 | St. Amand | |
| 4,338,826 A * | 7/1982 | Jacoby | G01N 1/24 |
| | | | 73/864.62 |
| D268,131 S | 3/1983 | St. Amand | |
| RE31,555 E | 4/1984 | Garren et al. | |
| 4,563,104 A | 1/1986 | Saint-Amand | |

(Continued)

FOREIGN PATENT DOCUMENTS

| | | |
|---|---|---|
| EP | 0796659 A2 | 9/1997 |
| JP | 10-245065 A | 9/1998 |

(Continued)

OTHER PUBLICATIONS

International Search Report from PCT App No. PCT/US2016/025022 dated Jul. 11, 2016, 1 pg.

*Primary Examiner* — Robert R Raevis

(74) *Attorney, Agent, or Firm* — Abel Law Group, LLP; Chi Suk Kim

(57) ABSTRACT

Embodiments of the present disclosure are directed to a small volume sampling device having a deformable fluid reservoir and a stem. The sampling device includes a plurality of volumetric fluid loading indicia increasing from the closed end of the deformable fluid reservoir to the open end of the deformable fluid reservoir adjacent the stem. The sampling device has an improved hold-up volume when sampling small volumes of fluid.

20 Claims, 2 Drawing Sheets

(56) References Cited

U.S. PATENT DOCUMENTS

| | | | |
|---|---|---|---|
| 4,563,332 A | 1/1986 | Mitchell et al. | |
| D299,956 S | 2/1989 | Saint-Amand | |
| 4,813,931 A * | 3/1989 | Hauze | A61M 1/0001 600/573 |
| D303,151 S | 8/1989 | Saint-Amand | |
| D303,152 S | 8/1989 | Saint-Amand | |
| 4,920,975 A | 5/1990 | Fay | |
| 5,073,347 A | 12/1991 | Garren et al. | |
| 5,132,232 A | 1/1992 | Parker | |
| 5,125,278 A | 6/1992 | Foldenauer | |
| D333,705 S | 3/1993 | Garren et al. | |
| D357,324 S | 4/1995 | Bartal | |
| D362,387 S | 9/1995 | Shumer | |
| D367,114 S | 2/1996 | Wilson et al. | |
| 5,624,554 A | 4/1997 | Falulkner et al. | |
| D385,793 S | 11/1997 | Marsal | |
| D401,698 S | 11/1998 | Daniels | |
| 5,916,813 A * | 6/1999 | Gorog | G01N 33/4905 422/504 |
| 5,919,146 A | 7/1999 | Propp | |
| D425,625 S | 5/2000 | Niermann | |
| 6,343,717 B1 | 2/2002 | Ihang et al. | |
| 6,357,626 B1 | 3/2002 | Zhang et al. | |
| 6,531,098 B1 | 3/2003 | Kenney | |
| D640,795 S | 6/2011 | Jackson et al. | |
| D640,796 S | 6/2011 | Wilkinson | |
| D650,088 S | 12/2011 | Motadel | |
| D659,848 S | 5/2012 | Termaat et al. | |
| D668,778 S | 10/2012 | Motadel | |
| D690,025 S | 9/2013 | Termaat et al. | |
| D694,424 S | 11/2013 | Kwak et al. | |
| D743,571 S | 11/2015 | Jackson et al. | |
| 2011/0129396 A1 | 6/2011 | Fish | |
| 2011/0212482 A1 | 9/2011 | Jangam et al. | |
| 2013/0344615 A1 | 12/2013 | Bodner et al. | |
| 2014/0186235 A1 | 7/2014 | Kwak et al. | |
| 2016/0288118 A1 * | 10/2016 | Profitt | B01L 3/021 |
| 2016/0324454 A1 * | 11/2016 | Bullington | A61B 5/157 |

FOREIGN PATENT DOCUMENTS

| | | |
|---|---|---|
| JP | 2003-012405 A | 1/2003 |
| WO | 2008143902 A2 | 11/2008 |

* cited by examiner

SMALL VOLUME SAMPLING DEVICE

CROSS-REFERENCE TO RELATED APPLICATION(S)

This application claims priority under 35 U.S.C. § 119(e) to U.S. Patent Application No. 62/150,530 entitled "SMALL VOLUME SAMPLING DEVICE," by Michael R. Huschke, filed Apr. 21, 2015, which is assigned to the current assignee hereof and incorporated herein by reference in its entirety.

FIELD OF THE DISCLOSURE

The present disclosure relates to small volume sampling devices, and more particularly to, disposable small volume sampling devices.

RELATED ART

State of the art sampling devices for sampling small volumes of liquid, such as in the range of from about 1 mL to about 30 mL, have substantial drawbacks. For example, state of the art devices are either too small to accommodate the required sampling volume or so large that there is an unacceptable amount of waste, such as in the form of hold-up volume. Moreover, state of the art devices are bulky and do not offer the ease of use, accuracy in measurements, or aseptic design demanded by the industry, and in particular the biopharmaceutical industry.

Accordingly, the present inventors surprisingly discovered a novel sampling device construction, certain embodiments of which have unexpectedly and significantly overcame these and other drawbacks.

BRIEF DESCRIPTION OF THE DRAWINGS

Embodiments are illustrated by way of example and are not limited in the accompanying figures.

Skilled artisans appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

DETAILED DESCRIPTION

The following description in combination with the figures is provided to assist in understanding the teachings disclosed herein. The following discussion will focus on specific implementations and embodiments of the teachings. This focus is provided to assist in describing the teachings and should not be interpreted as a limitation on the scope or applicability of the teachings. However, other embodiments can be used based on the teachings as disclosed in this application.

The terms "comprises," "comprising," "includes," "including," "has," "having" or any other variation thereof, are intended to cover a non-exclusive inclusion. For example, a method, article, or apparatus that comprises a list of features is not necessarily limited only to those features but may include other features not expressly listed or inherent to such method, article, or apparatus. Further, unless expressly stated to the contrary, "or" refers to an inclusive-or and not to an exclusive-or. For example, a condition A or B is satisfied by any one of the following: A is true (or present) and B is false (or not present), A is false (or not present) and B is true (or present), and both A and B are true (or present).

Also, the use of "a" or "an" is employed to describe elements and components described herein. This is done merely for convenience and to give a general sense of the scope of the invention. This description should be read to include one, at least one, or the singular as also including the plural, or vice versa, unless it is clear that it is meant otherwise. For example, when a single item is described herein, more than one item may be used in place of a single item. Similarly, where more than one item is described herein, a single item may be substituted for that more than one item.

Unless otherwise defined, all technical and scientific terms used herein have the same meaning as commonly understood by one of ordinary skill in the art to which this invention belongs. The materials, methods, and examples are illustrative only and not intended to be limiting. To the extent not described herein, many details regarding specific materials and processing acts are conventional and may be found in textbooks and other sources within the fluid transfer arts.

Embodiments of the present disclosure are directed to small volume sampling devices having improved workability including improvement measurement and reduced hold-up volumes for sampling small volumes of liquid. The concepts are better understood in view of the embodiments described below that illustrate and do not limit the scope of the present invention.

Figure 1:
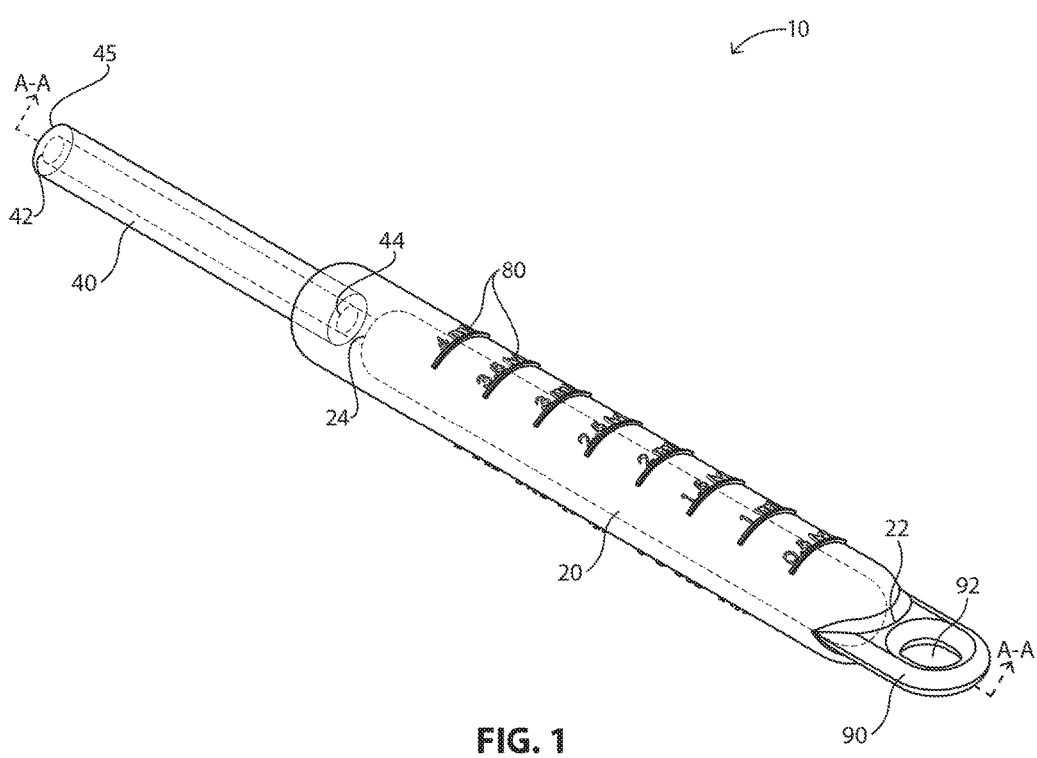
FIG. 1 includes an illustration of a perspective view of the sampling device of FIG. 1.
Figure 2:
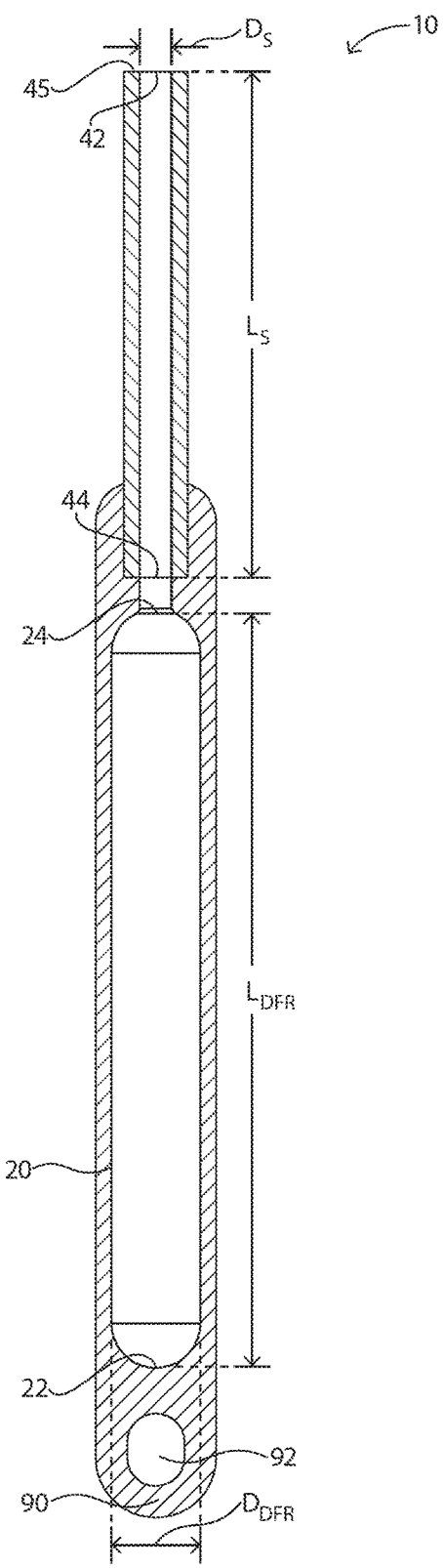
FIG. 2 includes an illustration of a cross-section view of a sampling device of FIG. 1 taken across cut line A-A.

Referring now to FIGS. 1 and 2, one embodiment of a sampling device can include a sampling device 10 having a deformable fluid reservoir 20 and a stem 40.

The deformable fluid reservoir 20 has a distal end 22 and a proximal end 24 opposite the distal end 22. The distal end 22 of the deformable fluid reservoir 20 can be closed, whereas the proximal end 24 of the deformable fluid reservoir 20 can be open and in fluid communication with the stem 40.

The stem 40 has a distal end 42 and a proximal end 44 opposite the distal end 42. The distal end 42 of the stem 40 can be open and form a tip 45 of the sampling device 10, and likewise, the proximal end 44 of the stem 40 can be open and in fluid communication with the proximal end 24 of the deformable fluid reservoir 20.

The sampling device 10 can be adapted to draw a fluid by squeezing the air out of the deformable fluid reservoir 20 and releasing the deformable fluid reservoir 20 while the tip 45 of the stem 40 is immersed in a fluid. Similarly, once fluid is retained within the deformable fluid reservoir 20, the fluid can be released by squeezing the deformable fluid reservoir 20 thereby forcing the fluid through the tip 45 and out of the sampling device 10.

In certain embodiments, the deformable fluid reservoir 20 can have a relatively low volumetric capacity. For example, in certain embodiments, the deformable fluid reservoir 20 can have a volumetric capacity of no greater than about 30 mL, no greater than about 25 mL, no greater than about 20 mL, no greater than about 15 mL, no greater than about 10 mL, no greater than about 9 mL, no greater than about 8 mL, no greater than about 7 mL, no greater than about 6 mL, or even no greater than about 5 mL. In further embodiments, the deformable fluid reservoir can have a volumetric capacity of at least about 0.1 mL, at least about 0.5 mL, or even at least about 1 mL. Moreover, the deformable fluid reservoir can have a volumetric capacity in a range of any of the minimums and maximums provided above, such as in a range of from about 0.1 mL to about 30 mL or even from about 1 mL to about 10 mL.

In certain embodiments, the sampling device 10 can include a plurality of indicia 80 that signifies a particular volumetric load of a fluid within the sampling device 10. For example, as illustrated in FIG. 1, the sampling device 10 can include a plurality of volumetric load indicia 80 disposed on the deformable fluid reservoir 20. The plurality of volumetric load indicia 80 can increase in the amount of volumetric load signified from the closed, distal end 22 of the deformable fluid reservoir 20 to the proximal end 24 of the deformable fluid reservoir. Accordingly, after an amount of fluid is drawn into the sampling device, measurement of the sample volume can be accomplished by inverting the sampling device 10 so that the closed, distal end 22 of the deformable fluid reservoir 20 points downward.

In particular embodiments, the deformable fluid reservoir 20 can have a generally consistent inner diameter over its length, $L_{DFR}$. In other words, the deformable fluid reservoir 20 can have a generally cylindrical shape as opposed to a bulbous shape.

Accordingly, in particular embodiments, the deformable fluid reservoir 20 can have a low standard deviation of its inner diameter over its length. In very particular embodiments, the deformable fluid reservoir can have a standard deviation of the average inner diameter over its length of no greater than about 10 mm, no greater than about 5 mm, no greater than about 3 mm, no greater than about 1 mm, no greater than about 0.5mm, no greater than about 0.3 mm, or even no greater than about 0.1 mm.

In certain embodiments, the deformable fluid reservoir 20 can have a desirable wall thickness. For example, in particular embodiments, the deformable fluid reservoir can have an average wall thickness of at least about 0.1 mm, at least about 0.2 mm, at least about 0.5 mm, or even at least about 1 mm. In further embodiments, the deformable fluid reservoir can have an average wall thickness of no greater than about 50 mm, no greater than about 40 mm, no greater than about 30 mm, or even no greater than about 20 mm. Moreover, the deformable fluid reservoir can have an average wall thickness in a range of any of the minimums and maximums provided above, such as in a range of from about 0.1 mm to about 50 mm, or even from about 1 mm to about 30 mm.

Referring in particular to FIG. 2, the deformable fluid reservoir 20 can have a particular length, $L_{DFR}$ and a particular width or diameter $D_{DFR}$. In certain embodiments, the sampling device 10 can have a desirable ratio of the length of the deformable fluid reservoir $L_{DFR}$ to the diameter of the deformable fluid reservoir $D_{DFR}$. For example, in particular embodiments, a ratio of the length of the deformable fluid reservoir to the diameter of the deformable fluid reservoir can be at least about 1.5:1, at least about 2:1, at least about 3:1, at least about 4:1, at least about 5:1, at least about 6:1, at least about 7:1, at least about 8:1, at least about 9:1, or even at least about 10:1. In further embodiments, a ratio of the length of the deformable fluid reservoir to the diameter of the deformable fluid reservoir can be no greater than about no greater than about 100:1, no greater than about 50:1, or even no greater than about 20:1. Moreover, a ratio of the length of the deformable fluid reservoir to the diameter of the deformable fluid reservoir can be in a range of any of the minimums and maximums provided above, such as in a range of from about 1.5:1 to about 100:1 or even from about 2:1 to about 50:1.

In certain embodiments, the stem 40 can have a desirable wall thickness. For example, in particular embodiments, the stem can have an average wall thickness of at least about 0.1 mm, at least about 0.2 mm, at least about 0.5 mm, or even at least about 1 mm. In further embodiments, the stem can have an average wall thickness of no greater than about 50 mm, no greater than about 40 mm, no greater than about 30 mm, or even no greater than about 20 mm. Moreover, the stem can have an average wall thickness in a range of any of the minimums and maximums provided above, such as in a range of from about 0.1 mm to about 50 mm, or even from about 1 mm to about 30 mm.

Similarly, the stem 40 can have a particular length, $L_S$ and a particular width or diameter $D_S$. In certain embodiments, the sampling device can have a desirable ratio of the length of the stem to the diameter of the stem. For example, in particular embodiments, a ratio of the length of the stem to the diameter of the stem can be at least about 1.5:1, at least about 2:1, at least about 3:1, at least about 4:1, at least about 5:1, at least about 6:1, at least about 7:1, at least about 8:1, at least about 9:1, or even at least about 10:1. In further embodiments, a ratio of the length of the stem to the diameter of the stem can be no greater than about no greater than about 100:1, no greater than about 50:1, or even no greater than about 20:1. Moreover, a ratio of the length of the stem to the diameter of the stem can be in a range of any of the minimums and maximums provided above, such as in a range of from about 1.5:1 to about 100:1 or even from about 2:1 to about 50:1.

In certain embodiments, the sampling device can have a desirable ratio of the length of the deformable fluid reservoir to the length of the stem. For example, in particular embodiments, a ratio of the length of the deformable fluid reservoir to the length of the stem can be at least about 1.1:1, at least about 1.2:1, or even at least about 1.4:1. In further embodiments, a ratio of the length of the deformable fluid reservoir to the length of the stem can be no greater than about 10:1, no greater than about 5:1, or even no greater than about 3:1. Moreover, a ratio of the length of the deformable fluid reservoir to the length of the stem can be in a range of any of the minimums and maximums provided above, such as in a range of from about 1.1:1 to about 10:1 or even from about 1.2:1 to about 5:1.

Referring again to FIG. 2, the deformable fluid reservoir can have a maximum inner diameter, and the stem can have a maximum inner diameter. In particular embodiments, the sampling device can have a desirable ratio of the maximum inner diameter of the deformable fluid reservoir to the maximum inner diameter of the stem. For example, a ratio of the maximum inner diameter of the deformable fluid reservoir to the maximum inner diameter of the stem can be at least about 1:1, at least about 1.1:1, at least about 1.2:1, at least about 1.3:1, or even at least about 1.5:1. In further embodiments, a ratio of the maximum inner diameter of the deformable fluid reservoir to the maximum inner diameter of the stem can be no greater than about 10:1, no greater than about 5:1, or even no greater than about 4:1. Moreover, a ratio of the maximum inner diameter of the deformable fluid reservoir to the maximum inner diameter of the stem can be in a range of any of the minimums and maximums provided above, such as in a range of from about 1:1 to about 10:1, or even from about 1.1:1 to about 5:1.

In certain embodiments, the deformable fluid reservoir 20, stem 40, and thus the sampling device 10, can have a desirable shape.

In particular embodiments, the deformable fluid reservoir 20 can have a generally cylindrical shape. For example, the deformable fluid reservoir 20 can a substantially constant inner and/or outer diameter, not including the tapered portions at the distal and proximal ends.

In further embodiments, the stem 40 can have a generally cylindrical shape. For example, the stem 40 can have a substantially constant inner and/or outer diameter.

In particular embodiments, both the deformable fluid reservoir 20 and the stem 40 can have a generally cylindrical shape. Accordingly, in certain embodiments, the sampling device can have a generally cylindrical shape, such as a two step cylindrical shape, where the inner diameter of the deformable fluid reservoir is greater than the inner diameter of the stem.

In certain embodiments, the deformable fluid reservoir 20 can be composed of a desired material. For example, in particular embodiments, the deformable fluid reservoir 20 can be composed of a polymeric based material. In very particular embodiments, the deformable fluid reservoir 20 can be composed of a silicone based material, a thermoplastic based material such as a thermoplastic elastomer based material, or a combination thereof.

In certain embodiments, the polymeric based material composing the deformable fluid reservoir can have particular characteristics, such as, for example, an advantageous softness, transparency, clarity, or combinations thereof.

In particular embodiments, the polymeric based material composing the fluid reservoir can have an advantageous softness. As used herein, softness (or likewise hardness) is measured according to ASTM D2240-02 as is well understood in the art. Accordingly, in particular embodiments, the polymeric based material composing the deformable fluid reservoir can have a softness of at least about 10 Durometer, at least about 15 Durometer, at least about 20 Durometer, or even at least about 25 Durometer. In further embodiments, the polymeric based material composing the deformable fluid reservoir can have a softness of no greater than about 90 Durometer, no greater than about 85 Durometer, no greater than about 80 Durometer, or even no greater than about 75 Durometer. Moreover, the polymeric based material composing the deformable fluid reservoir can have a softness in a range of any of the minimums and maximums provided above, such as in a range of from about 10 Durometer to about 90 Durometer, or even from about 20 Durometer to about 80 Durometer.

In particular embodiments, the deformable fluid reservoir 20 can have a greater softness (or less hardness) than the stem 40. For example, in certain embodiments, the fluid reservoir 20 can be deformable, whereas the stem 40 is generally non-deformable by application of equivalent forces.

In certain embodiments, the sampling device, and in particular, the deformable fluid reservoir can have a desirable transparency and clarity. For example, it can be advantageous for the fluid within the deformable fluid reservoir be visible for ease of measurement.

Referring again to FIGS. 1 and 2, the sampling device can include a tab portion 90 extending axially from the distal end 22 of the deformable fluid reservoir 20. The tab portion 90 can include an aperture 92 formed within the tab portion 90. The end tab 90 with the aperture 92 can be adapted to allow the sampling device 10 to be hung, such as for display or for in use in a laboratory setting for quick access and easy storage.

In certain embodiments, the sampling device 10 can be sterilizable. As used herein, the phrase "sterilizable" refers to a sampling device which can be sterilized without detrimentally impairing the use of the sampling device and remaining essentially inert to a fluid being sampled. For example, certain materials, such as silicone or certain thermoplastics, such as a thermoplastic elastomer, for example C-Flex®, can withstand the temperatures and pressures of sterilization and therefore are sterilizable.

Similarly, the sampling device can be sterilizable by autoclave or autoclavable. As used herein, the phrase "sterilizable by autoclave" or "autoclavable" refers to a sampling device which can be sterilized in an autoclave without detrimentally impairing the use of the sampling device and remaining essentially inert to a fluid being sampled. For example, certain materials, such as silicone or certain thermoplastics, such as a thermoplastic elastomer, for example C-Flex®, can withstand the temperatures and pressures of autoclave sterilization and therefore are sterilizable by autoclave.

In certain embodiments, the sampling device 10 can be a single piece, also referred to as monolithic. For example, as will be discussed in more detail below, the sampling device 10 can be unitarily formed by molding. As another example, the stem 40 can be separately formed and the deformable fluid reservoir 20 overmolded onto the stem 20 to form a monolithic sampling device.

In certain embodiments, the sampling device 10 can be disposable. For example, the sampling device 10 can be adapted to be disposed after use, otherwise referred to as "single-use".

In certain embodiments, the deformable fluid reservoir 20 can be covalently bonded to the stem. For example, as described above, the sampling device 10 can be unitarily formed, such as from the same material in a single molding operation. Accordingly, the deformable fluid reservoir 20 would be covalently bonded to the stem 40. As another example, as described above, the sampling device 10 can include a separately formed stem 40 and a deformable fluid reservoir 20 overmolded onto the stem 40. If the materials are compatible, the deformable fluid reservoir 20 can be covalently bonded to the stem.

Another aspect of the present disclosure is directed to a method of forming a sampling device. It is to be understood that any of the characteristics of the sampling device and its components described above are equally applicable to aspects of the disclosure directed to methods of forming a sampling device.

In general, a method of forming a sampling device can include: providing a polymeric resin; and forming a sampling device as described in any of the embodiments described herein.

In particular embodiments, forming the sampling device can include a molding operation, such as blow molding, injection molding, overmolding, or any combination thereof.

In particular embodiments, the mold can include elements to form the volumetric load indicia, such that the volumetric load indicia are simultaneously formed with the formation of the sampling device, and in particular, simultaneously formed with the formation of the deformable fluid reservoir. In other embodiments, the volumetric load indicia can be formed onto the deformable fluid reservoir after formation of the deformable fluid reservoir, such as for example by etching, stamping, or printing.

The present disclosure represents a departure from the state of the art. For example, certain embodiments of the present disclosure describe a small volume sampling device that has unique dimensional features and material characteristics that allow for easy handling, accurate measurements, reduced hold-up volumes, sterilizable sampling devices, or combinations thereof. Furthermore, employing a plurality of volumetric loading indicia as described herein is a unique arrangement for such small volume sampling devices. Compared to state of the art devices which are either to small to hold the desired volume of fluid or so big that they have substantial hold up volume and unnecessary capacity and expense, the sampling devices of the present disclosure offer a unique construction with unparalleled efficacy in sampling small volumes of fluid, particularly in a pharmaceutical or other industry involving sensitive fluids.

Many different aspects and embodiments are possible. Some of those aspects and embodiments are described below. After reading this specification, skilled artisans will appreciate that those aspects and embodiments are only illustrative and do not limit the scope of the present invention. Embodiments may be in accordance with any one or more of the items as listed below.

Item 1. A sampling device comprising:
 a. a deformable fluid reservoir having a closed distal end and an open proximal end opposite the closed distal end; and
 b. a stem having an open distal end and an open proximal end opposite the distal end, wherein the open proximal end is in fluid communication with the open proximal end of the deformable fluid reservoir;
 c. wherein the deformable fluid reservoir and stem are covalently bonded to each other;
 d. wherein the sampling device has a volumetric capacity of no greater than about 30 mL; and
 e. wherein the deformable fluid reservoir comprises a plurality of volumetric indicia increasing in identification of volumetric loading from the distal end of the deformable fluid reservoir to the proximal end of the deformable fluid reservoir.

Item 2. The sampling device of any one of the preceding items, wherein the sampling device is adapted to identify a volumetric loading of a fluid when inverted such that the closed distal end of the sampling device is pointed downward and the sampling device extends vertically.

Item 3. The sampling device of any one of the preceding items, wherein the deformable fluid reservoir has a volumetric capacity of at least about 0.1 mL, at least about 0.5 mL, or even at least about 1 mL.

Item 4. The sampling device of any one of the preceding items, wherein the deformable fluid reservoir has a volumetric capacity of no greater than about 30 mL, no greater than about 25 mL, no greater than about 20 mL, no greater than about 15 mL, no greater than about 10 mL, no greater than about 9 mL, no greater than about 8 mL, no greater than about 7 mL, no greater than about 6 mL, or even no greater than about 5 mL.

Item 5. The sampling device of any one of the preceding items, wherein the deformable fluid reservoir has a volumetric capacity in a range of from about 0.1 mL to about 30 mL or even from about 1 mL to about 10 mL.

Item 6. The sampling device of any one of the preceding items, wherein the deformable fluid reservoir is flexible.

Item 7. The sampling device of any one of the preceding items, wherein the deformable fluid reservoir has a softness of at least about 10 Durometer, at least about 15 Durometer, at least about 20 Durometer, or even at least about 25 Durometer as measured according to measured according to ASTM D2240-02.

Item 8. The sampling device of any one of the preceding items, wherein the deformable fluid reservoir has a softness of no greater than about 90 Durometer, no greater than about 85 Durometer, no greater than about 80 Durometer, or even no greater than about 75 Durometer.

Item 9. The sampling device of any one of the preceding items, wherein the deformable fluid reservoir has a softness in a range of from about 10 Durometer to about 90 Durometer, or even from about 20 Durometer to about 80 Durometer.

Item 10. The sampling device of any one of the preceding items, wherein the deformable fluid reservoir is adapted to draw and release a fluid by squeezing the deformable fluid reservoir.

Item 11. The sampling device of any one of the preceding items, wherein the deformable fluid reservoir has a greater flexibility than the stem.

Item 12. The sampling device of any one of the preceding items, wherein the sampling device is composed of a plastic based material.

Item 13. The sampling device of any one of the preceding items, wherein the sampling device is composed of a silicone based material, a thermoplastic based material such as a thermoplastic elastomer based material, or a combination thereof.

Item 14. The sampling device of any one of the preceding items, wherein the deformable fluid reservoir has a standard deviation of its average inner diameter over its length of no greater than about 10 mm, no greater than about 5 mm, no greater than about 3 mm, no greater than about 1 mm, no greater than about 0.5mm, no greater than about 0.3 mm, or even no greater than about 0.1 mm.

Item 15. The sampling device of any one of the preceding items, wherein the sampling device is sterilizable.

Item 16. The sampling device of any one of the preceding items, wherein the sampling device is autoclavable.

Item 17. The sampling device of any one of the preceding items, wherein the sampling device is formed by molding and curing a resin about a mandrel.

Item 18. The sampling device of any one of the preceding items, wherein the deformable fluid reservoir has a length and a diameter, and wherein the length is greater than the diameter.

Item 19. The sampling device of any one of the preceding items, wherein a ratio of the length of the deformable fluid reservoir to the diameter of the deformable fluid reservoir is at least about 1.5:1, at least about 2:1, at least about 3:1, at least about 4:1, at least about 5:1, at least about 6:1, at least about 7:1, at least about 8:1, at least about 9:1, or even at least about 10:1.

Item 20. The sampling device of any one of the preceding items, wherein a ratio of the length of the deformable fluid reservoir to the diameter of the deformable fluid reservoir is no greater than about 100:1, no greater than about 50:1, or even no greater than about 20:1.

Item 21. The sampling device of any one of the preceding items, wherein the deformable fluid reservoir is generally cylindrical.

Item 22. The sampling device of any one of the preceding items, wherein the deformable fluid reservoir has an average wall thickness of at least about 0.1 mm, at least about 0.2 mm, at least about 0.5 mm, or even at least about 1 mm.

Item 23. The sampling device of any one of the preceding items, wherein the deformable fluid reservoir has an average wall thickness of no greater than about 50 mm, no greater than about 40 mm, no greater than about 30 mm, or even no greater than about 20 mm.

Item 24. The sampling device of any one of the preceding items, wherein the deformable fluid reservoir has an average wall thickness in a range of from about 0.1 mm to about 50 mm, or even from about 1 mm to about 30 mm.

Item 25. The sampling device of any one of the preceding items, wherein the stem has a length and a diameter, and wherein the length is greater than the diameter.

Item 26. The sampling device of any one of the preceding items, wherein a ratio of the length of the stem to the diameter of the stem is at least about 1.5:1, at least about 2:1, at least about 3:1, at least about 4:1, at least about 5:1, at least about 6:1, at least about 7:1, at least about 8:1, at least about 9:1, or even at least about 10:1.

Item 27. The sampling device of any one of the preceding items, wherein a ratio of the length of the stem to the diameter of the stem is no greater than about 100:1, no greater than about 50:1, or even no greater than about 20:1.

Item 28. The sampling device of any one of the preceding items, wherein the stem is generally cylindrical.

Item 29. The sampling device of any one of the preceding items, wherein the stem has an average wall thickness of at least about 0.1 mm, at least about 0.2 mm, at least about 0.5 mm, or even at least about 1 mm.

Item 30. The sampling device of any one of the preceding items, wherein the stem has an average wall thickness of no greater than about 50 mm, no greater than about 40 mm, no greater than about 30 mm, or even no greater than about 20 mm.

Item 31. The sampling device of any one of the preceding items, wherein the stem has an average wall thickness in a range of from about 0.1 mm to about 50 mm, or even from about 1 mm to about 30 mm.

Item 32. The sampling device of any one of the preceding items, wherein the stem is generally cylindrical.

Item 33. The sampling device of any of the preceding items, wherein the length of the deformable fluid reservoir is greater than the length of the stem.

Item 34. The sampling device of any one of the preceding items, wherein a ratio of the length of the deformable fluid reservoir to the length of the stem is at least about 1.1:1, at least about 1.2:1, or even at least about 1.4:1.

Item 35. The sampling device of any one of the preceding items, wherein a ratio of the length of the deformable fluid reservoir to the length of the stem is no greater than about 10:1, no greater than about 5:1, or even no greater than about 3:1.

Item 36. The sampling device of any one of the preceding items, wherein a ratio of the length of the deformable fluid reservoir to the length of the stem is in a range of from about 1.1:1 to about 10:1 or even from about 1.2:1 to about 5:1.

Item 37. The sampling device of any one of the preceding items, wherein the deformable fluid reservoir has a maximum inner diameter and a maximum outer diameter, wherein the outer diameter of the deformable fluid reservoir defines an outer surface of the sampling device, wherein the stem has a maximum inner diameter and a maximum outer diameter, wherein the outer diameter of the stem defines an outer surface of the sampling device, and wherein a ratio of the maximum inner diameter of the deformable fluid reservoir to the maximum inner diameter of the stem is at least about 1:1, at least about 1.1:1, at least about 1.2:1, at least about 1.3:1, or even at least about 1.5:1.

Item 38. The sampling device of any one of the preceding items, wherein a ratio of the maximum inner diameter of the deformable fluid reservoir to the maximum inner diameter of the stem is no greater than about 10:1, no greater than about 5:1, or even no greater than about 4:1.

Item 39. The sampling device of any one of the preceding items, wherein a ratio of the maximum inner diameter of the deformable fluid reservoir to the maximum inner diameter of the stem is in a range of from about 1:1 to about 10:1, or even from about 1.1:1 to about 5:1.

Item 40. The sampling device of any one of the preceding items, wherein the sampling device further comprises a tab adjacent the deformable fluid reservoir at the distal end.

Item 41. The device of any one of the preceding items, wherein the tab comprises an aperture.

Item 42. The sampling device of any one of the preceding items, wherein the sampling device is monolithic.

Item 43. The sampling device of any one of the preceding items, wherein the deformable fluid reservoir is monolithic with the stem.

Item 44. The sampling device of any one of the preceding items, wherein the deformable fluid reservoir and stem are composed of essentially the same material.

Note that not all of the activities described above in the general description or the examples are required, that a portion of a specific activity may not be required, and that one or more further activities may be performed in addition to those described. Still further, the order in which activities are listed is not necessarily the order in which they are performed.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

The specification and illustrations of the embodiments described herein are intended to provide a general understanding of the structure of the various embodiments. The specification and illustrations are not intended to serve as an exhaustive and comprehensive description of all of the elements and features of apparatus and systems that use the structures or methods described herein. Separate embodiments may also be provided in combination in a single embodiment, and conversely, various features that are, for brevity, described in the context of a single embodiment, may also be provided separately or in any subcombination. Further, reference to values stated in ranges includes each and every value within that range. Many other embodiments may be apparent to skilled artisans only after reading this specification. Other embodiments may be used and derived from the disclosure, such that a structural substitution, logical substitution, or another change may be made without departing from the scope of the disclosure. Accordingly, the disclosure is to be regarded as illustrative rather than restrictive.

What is claimed is:
1. A sampling device comprising:
  a. a deformable fluid reservoir having a closed distal end and an open proximal end opposite the closed distal end; and
  b. a stem having an open distal end and an open proximal end opposite the distal end, wherein the open proximal end is in fluid communication with the open proximal end of the deformable fluid reservoir;
  c. wherein the deformable fluid reservoir and stem are covalently bonded to each other;

d. wherein the sampling device has a volumetric capacity of no greater than about 30 mL; and e. wherein the deformable fluid reservoir comprises a plurality of volumetric indicia increasing in identification of volumetric loading from the distal end of the deformable fluid reservoir to the proximal end of the deformable fluid reservoir.

2. The sampling device of claim 1, wherein the sampling device is adapted to identify a volumetric loading of a fluid when inverted such that the closed distal end of the sampling device is pointed downward and the sampling device extends vertically.

3. The sampling device of claim 1, wherein the deformable fluid reservoir has a volumetric capacity in a range of from about 1 mL to about 30 mL.

4. The sampling device of claim 1, wherein the deformable fluid reservoir has a softness in a range of from about 10 Durometer to about 90 Durometer.

5. The sampling device of claim 1, wherein the deformable fluid reservoir is adapted to draw and release a fluid by squeezing the deformable fluid reservoir.

6. The sampling device of claim 1, wherein the deformable fluid reservoir has a greater flexibility than the stem.

7. The sampling device of claim 1, wherein the deformable fluid reservoir has a standard deviation of its average inner diameter over its length of no greater than about 5 mm.

8. The sampling device of claim 1, wherein the sampling device is autoclavable.

9. The sampling device of claim 1, wherein the deformable fluid reservoir has a length and a diameter, and wherein the length is greater than the diameter.

10. The sampling device of claim 1, wherein a ratio of the length of the deformable fluid reservoir to the diameter of the deformable fluid reservoir is at least about 1.5:1 and no greater than about 20:1.

11. The sampling device of claim 1, wherein the deformable fluid reservoir is generally cylindrical.

12. The sampling device of claim 1, wherein the deformable fluid reservoir has an average wall thickness in a range of from about 1 mm to about 30 mm.

13. The sampling device of claim 1, wherein the stem has a length and a diameter, wherein a ratio of the length of the stem to the diameter of the stem is at least about 1.5:1 and no greater than about 20:1.

14. The sampling device of claim 1, wherein the stem is generally cylindrical.

15. The sampling device of claim 1, wherein the stem has an average wall thickness in a range of from about 1 mm to about 30 mm.

16. The sampling device of claim 1, wherein the length of the deformable fluid reservoir is greater than the length of the stem.

17. The sampling device of claim 1, wherein a ratio of the length of the deformable fluid reservoir to the length of the stem is in a range of from about 1.1:1 to about 10:1.

18. The sampling device of claim 1, wherein the deformable fluid reservoir has a maximum inner diameter and a maximum outer diameter, wherein the outer diameter of the deformable fluid reservoir defines an outer surface of the sampling device, wherein the stem has a maximum inner diameter and a maximum outer diameter, wherein the outer diameter of the stem defines an outer surface of the sampling device, and wherein a ratio of the maximum inner diameter of the deformable fluid reservoir to the maximum inner diameter of the stem is in a range of from about 1:1 to about 10:1.

19. The sampling device of claim 1, wherein the sampling device further comprises a tab adjacent the deformable fluid reservoir at the distal end.

20. The sampling device of claim 1, wherein the deformable fluid reservoir is monolithic with the stem.

* * * * *